(12) United States Patent
Mäntylä

(10) Patent No.: US 9,151,710 B2
(45) Date of Patent: Oct. 6, 2015

(54) MOISTURE MEASUREMENT

(71) Applicant: METSO AUTOMATION OY, Vantaa (FI)

(72) Inventor: Markku Mäntylä, Kangasala (FI)

(73) Assignee: Valmet Automation OY, Vantaa (FI)

( * ) Notice: Subject to any disclaimer, the term of this patent is extended or adjusted under 35 U.S.C. 154(b) by 0 days.

(21) Appl. No.: 14/403,650

(22) PCT Filed: May 22, 2013

(86) PCT No.: PCT/FI2013/050560
§ 371 (c)(1),
(2) Date: Nov. 25, 2014

(87) PCT Pub. No.: WO2013/175072
PCT Pub. Date: Nov. 28, 2013

(65) Prior Publication Data
US 2015/0153273 A1    Jun. 4, 2015

(30) Foreign Application Priority Data

May 25, 2012  (FI) ..................................... 20125561

(51) Int. Cl.
*G01J 5/02*      (2006.01)
*G01N 21/3559*   (2014.01)
(Continued)

(52) U.S. Cl.
CPC ............ *G01N 21/3559* (2013.01); *G01N 21/86* (2013.01); *G01N 2021/3148* (2013.01); *G01N 2021/8663* (2013.01); *G01N 2201/062* (2013.01); *G01N 2201/06113* (2013.01)

(58) Field of Classification Search
CPC ............ G01N 21/3554; G01N 33/346; G01N 2021/8917; G01N 2021/3166; G01N 21/35; G01N 23/16; G01N 33/34
See application file for complete search history.

(56) References Cited

U.S. PATENT DOCUMENTS 3,792,271 A * 2/1974 Sandblom ..................... 250/347
4,300,049 A   11/1981 Sturm
(Continued)

FOREIGN PATENT DOCUMENTS

DE   10 2004 060 036 A1   6/2006
EP          0332018 A2    9/1989
(Continued)

OTHER PUBLICATIONS

Jun. 3, 2014 Search Report issued in Finnish Application No. 20125561.
(Continued)

*Primary Examiner* — Kiho Kim
(74) *Attorney, Agent, or Firm* — Oliff PLC

(57) ABSTRACT

Detector receives optical radiation transmitted through measured object and is responsive to one or more predetermined optical absorption bands of water and cellulose and two or more separate optical bands related to spectral disturbance caused by coloring substance. The measuring unit measures, on basis of responses of the detector, a water dependent value on basis of attenuation of optical radiation in predetermined optical absorption band of water, a cellulose dependent value on basis of attenuation of optical radiation in predetermined optical absorption band of cellulose, determines general dependence of attenuation with respect to wavelength including spectral disturbance caused by coloring substance by measuring attenuations in predetermined separate optical bands apart from predetermined bands of water and cellulose, and forms a moisture value on basis of moisture dependent value, cellulose dependent value, and general dependence of attenuation for compensating for spectral disturbance of at least one coloring substance.

21 Claims, 8 Drawing Sheets

(51) Int. Cl.
  *G01N 21/31* (2006.01)
  *G01N 21/86* (2006.01)

(56) References Cited

U.S. PATENT DOCUMENTS

| | | | |
|---|---|---|---|
| 4,306,151 A | | 12/1981 | Chase |
| 4,707,603 A | | 11/1987 | Miemela et al. |
| 4,805,623 A | | 2/1989 | Jobsis |
| 4,845,730 A | * | 7/1989 | Mercer ............................ 378/53 |
| 5,124,552 A | * | 6/1992 | Anderson ................ 250/339.04 |
| 5,250,811 A | | 10/1993 | Lippert et al. |
| 5,276,327 A | | 1/1994 | Bossen et al. |
| 6,281,498 B1 | | 8/2001 | Fellows |
| 6,355,931 B1 | | 3/2002 | Hernandez et al. |
| 6,495,831 B1 | | 12/2002 | Hyvarinen et al. |
| 6,526,369 B1 | | 2/2003 | Meinecke et al. |
| 2003/0047135 A1 | | 3/2003 | Kansakoski et al. |
| 2005/0155735 A1 | | 7/2005 | Ischdonat et al. |
| 2009/0185162 A1 | | 7/2009 | Shakespeare et al. |

FOREIGN PATENT DOCUMENTS

| | | |
|---|---|---|
| EP | 0 380 412 A2 | 8/1990 |
| GB | 2044443 A | 10/1980 |
| WO | 2011135179 A1 | 11/2011 |
| WO | 2012057699 A1 | 5/2012 |

OTHER PUBLICATIONS

Sep. 9, 2013 Search Report issued in International Application No. PCT/FI2013/050560.

Aug. 26, 2014 International Preliminary Report on Patentability issued in International Application No. PCT/FI2013/050560.

Dumont et al., "Estimation of Moisture Variations on Paper Machines," IEEE Transactions on Control Systems, Jun. 1993, No. 2, pp. 101-112.

Pover et al., "NIR-Feuchteanalysatoren fü berahrungslose On-line-Messungen unter Produktionsbedingungen," TM Technisches Messen, Mar. 1992, No. 3, pp. 116-120.

May 7, 2015 Extended Search Report issued in European Application No. 13793944.3.

\* cited by examiner

MOISTURE MEASUREMENT

FIELD

The invention relates to a moisture measurement.

BACKGROUND

Moisture content of paper may be measured by directing infrared light from an optical source to the paper. Interaction between the paper and the infrared light attenuates the power of the infrared light. For example, water attenuates strongly at known, narrow optical bands in infrared region. The attenuation of water depends on the amount of the water in the paper. When an attenuation of an absorption band of water is measured, it is possible to determine moisture content of the measured paper.

When paper comprises colorants such as ink on the surface or inside the sheet the measurement faces serious problems and fails to provide reliable results. Hence, there is a need for a better measurement.

SUMMARY

The following presents a simplified summary of the invention in order to provide a basic understanding of some aspects of the invention. Its purpose is to present some concepts of the invention in a simplified form as a prelude to the more detailed description that is presented later.

An aspect of the invention relates to apparatus of claim 22.
An aspect of the invention relates to system of claim 29.
An aspect of the invention relates to system of claim 30.
An aspect of the invention relates to method of claim 31.
An aspect of the invention relates to method of claim 37.
An aspect of the invention relates to a method of claim 38.
An aspect of the invention relates to apparatus of claim 39.
An aspect of the invention relates to a system of claim 41.
An aspect of the invention relates to system of claim 42.

Although the various aspects, embodiments and features of the invention are recited independently, it should be appreciated that all combinations of the various aspects, embodiments and features of the invention are possible and within the scope of the present invention as claimed.

The present solution provides advantages. An optical moisture measurement becomes possible and accurate when measuring an object including at least one coloring substance and cellulose. The process control of the measured object may also be enhanced on the basis of the measurement.

BRIEF DESCRIPTION OF THE DRAWINGS

In the following the invention will be described in greater detail by means of exemplary embodiments with reference to the attached drawings, in which.

DESCRIPTION OF EMBODIMENTS

Exemplary embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

Figure 1:
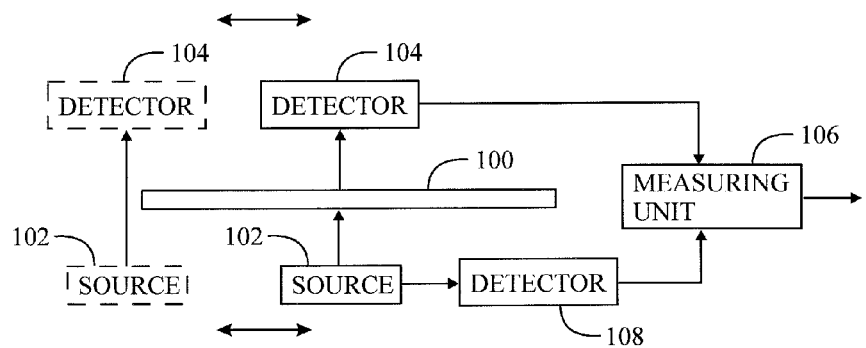
FIG. 1 shows a measurement configuration.

FIG. 1 presents a principle of a measurement configuration. A measured object 100 comprising cellulose material and coloring substance is placed between an optical source 102 outputting optical radiation and a detector 104 receiving the optical radiation after interaction with the sheet 100. The detector 104 and the measuring unit 106 may be parts of a measuring device which may also comprise the optical source 102.

The measured object 100 may be a sheet of paper, for example. The cellulose material of the measured object 100 may be in wood fibers which may be raw material of the measured object 100. The coloring substance may one or more colorants or tones. The coloring substance may be ink used to print readable characters such as alpha numeric signs and/or images on the measured object 100. The readable characters and/or images may be visible and recognizable on the measured object 100 when the measurement is made. Alternatively, the coloring substance may be mixed and/or scattered within the material of the measured object 100 which may take place when the sheet of a colored paper or a sheet made of recycled paper is measured, for example. The coloring substance may be a gravure ink or a relief printing ink, for example.

The optical source 102 may output a broad and continuous band of radiation. The output optical band may comprise the infrared region including wavelengths between about 750 nm to 500 μm. In an embodiment the optical band of the optical source 102 comprises a near infrared, a short-wavelength infrared and mid-wavelength infrared regions including wavelengths between about 750 nm to 10 μm, for example. Instead of continuous band the optical source 102 may output at least two discrete optical bands in the measured optical bands. The optical source 102 may comprise an incandescent lamp, a light-emitting diode (LED), a laser, a gas discharge lamp or the like, for example. The optical source 102 may additionally comprise at least one optical component for changing the shape of the beam of the light and or directing the beam of light to the measured object 100. The at least one optical component may be a lens, a mirror, a beam splitter/combiner, an optical filter, optical fiber or the like.

The detector 104 receives optical radiation transmitted through the measured object 100 comprising cellulose material. The detector 104 outputs electrical signals in response to detected powers of the measured optical bands such that the detector 104 is responsive to one or more predetermined optical absorption bands of water, one or more predetermined optical absorption bands cellulose and two or more separate optical bands apart from the predetermined optical absorption bands. A predetermined absorption band means an optical band associated with an absolute or a local maximum in the absorption curve. That an optical band is associated with the maximum absorption means that at least one wavelength in the known absorption band is detected. The at least one wavelength may comprise the wavelength with the strongest absorption in the detected band or the at least one wavelength may comprise one or more other wavelengths of the known absorption band.

The output power or the power distribution as a function of wavelength may be measured by taking a sample from the output optical radiation by the detector 104 when the measured object 100 is not between the optical source 102 and the detector 104. The measurement may be performed such that the detector 104 and the optical source 102 move over the edge of the measured object (shown in dashed lines). In a traversing measurement that may be performed after each traverse or from time to time. The measurement without the measured object 100 defines a reference optical power $I_0$ in each measured band $\Delta\lambda i$ directed to the measured object 100. In this way, the whole optical path can be measured.

In an embodiment, a detector 108 similar to the detector 104 may be used to take a sample of the output optical radiation of the optical source 102 for an alternative or additional reference optical power $I_0$. The sample of the output optical radiation may mean some known percentages of the output optical radiation of the source 102, for example. For instance, about 95% of each wavelength may proceed to the measured object 100 and 5% may be directed to the detector 108 by a beam splitter.

Additionally or alternatively, the power or the power distribution may be known beforehand since certain types of optical sources (such as lasers) may output a known optical power or a known optical power distribution in a known optical band. Hence, the sampling of the output optical power of the optical source 102 is not presented in more detail.

The detector 104 may comprise one or more detecting elements. The detector 104 may be based on a semi-conductor technology. The detector 104 may comprise at least one photo diode such as a PIN diode, an avalanche diode or the like. The detecting elements of the detector 104 may be arranged in an array or in a matrix. The detector 104 having a plurality of detecting elements may be comprise discrete elements or they may be integrated together using IC-technology (Integrated Circuit). The matrix of elements of the detector 104 may be based on a InGaAs (Indium Gallium Arsenide), extended InGaAs, HgCdTe (Mercury Cadmium Telluride), PbS (Lead Sulfide), PbSe (Lead Selenide) technique in the infrared region, for example. The detector 104 may detect different optical bands simultaneously such that different detecting elements detect different optical bands at the same time. Alternatively or additionally, the detector 104 may detect at least one optical band temporally successively with respect to at least one other optical band.

The detector 104 may additionally comprise at least one optical component for changing the shape of the beam of the light and/or directing the beam of light to the at least one detecting element. The at least one optical component may be a lens, a mirror, a beam splitter/combiner, an optical filter, optical fiber or the like.

On the basis of responses of the detector 104, the measuring unit 106 measures several parameters of the detected bands of the optical radiation. The detector 104 and the measuring unit 106 together form an optical power meter measuring optical power as a function of wavelength. The measuring unit 106 may comprise at least one processor, at least one memory and at least one computer program for processing the measured data. In an embodiment, the detector 104 and at least one suitable computer program comprise the measuring device, since the at least one computer program may be loaded in an otherwise existing system associated with a paper machine or a printing machine for processing the data fed from the detector 104.

Figure 2A:
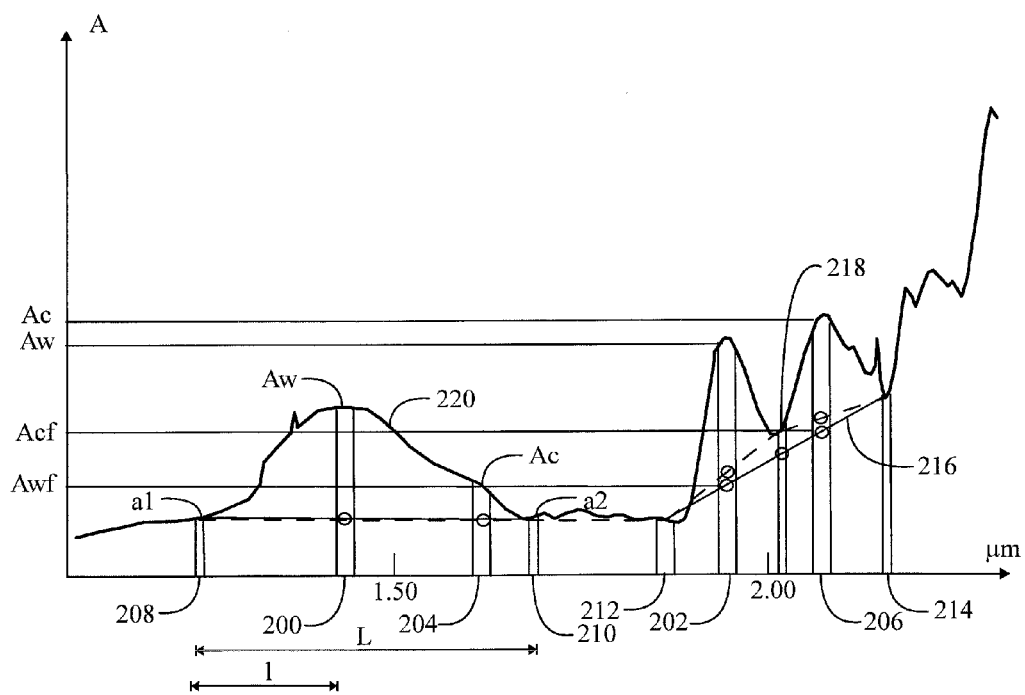
FIG. 2A shows attenuation as function of wavelength.

The following explains the operation of the measuring unit 106 with the help of FIG. 2A. The measuring unit 106 measures at least one water dependent value Aw on the basis of attenuation of the optical radiation in the one or more predetermined optical absorption bands 200, 202 of water. The attenuation is a linearized reciprocal value with respect to transmittance of the object 100. However, they both imply the same property and may be referred to as attenuation. Similarly, the measuring unit 106 measures at least one cellulose dependent value Ac on the basis of attenuation of the optical radiation at the one or more predetermined optical absorption bands 204, 206 of cellulose. The water dependent value Aw of each band 200, 202 may be related to an optical power integrated over the optical band 200, 202. Correspondingly, other measured values may be formed by integrating over the measured band.

The attenuation of a measured band $\Delta\lambda i$, where i refers to index of a band and $\Delta\lambda$ refers to wavelength range in the band i, may be measured by comparing the optical power $I_{0,\Delta\lambda i}$ directed to the measured object 100 and the optical power $I_{\Delta\lambda i}$ received by the detector 104. A measured band $\Delta\lambda i$ may comprise monochromatic optical radiation or a continuous wavelength range. Attenuation $A_i$, which may be interpreted as absorbance, in each optical band i may then be determined as:

$$A_i = -\log(I_{\Delta\lambda,i}/I_{0,\Delta\lambda,i}).$$

More accurately the attenuation $A_i$ may be solved from an equation $I_{\Delta\lambda,i} = I_{0,\Delta\lambda,i} \exp{-(\sum_{j=1}^{N} as_j + \sum_{j=1}^{N} aa_j)x}$, where exp is an exponential function based on Euler's number (about 2.71828) or 10, for example, j is the index of an substance in the measured object 100, N is the number of substances, $as_j$ is a scattering coefficient, $aa_j$ is an absorption coefficient and x is a traveled distance of the optical radiation in the measured object 100. The term $I_{0,\Delta\lambda,i}$ may often be ignored such that its value may be assumed as 1, for instance. The coefficients $as_j$ and $aa_j$, depend on the concentration of the substance j. Since the distance x may be ignored, the measured attenuation $A_i$ is a function of the sum of the scattering coefficients $\sum_{j=1}^{N} as_j$ and the sum of absorption coefficients $\sum_{j=1}^{N} aa_j$, $A_i = -\log(I_{\Delta\lambda,i}/I_{0,\Delta\lambda,i}) = (\sum_{j=1}^{N} as_j + \sum_{j=1}^{N} aa_j)$ where the logarithmic function is based on Euler's number or 10, for example. In the measurement, attenuations of water and cellulose material are measured. However, other substances such as coloring materials cause a general wavelength dependence which may disturb the measurement of attenuation and result in displacement and tilt of attenuation curve with respect to a measurement performed with a sample without the coloring materials.

Figure 2B:
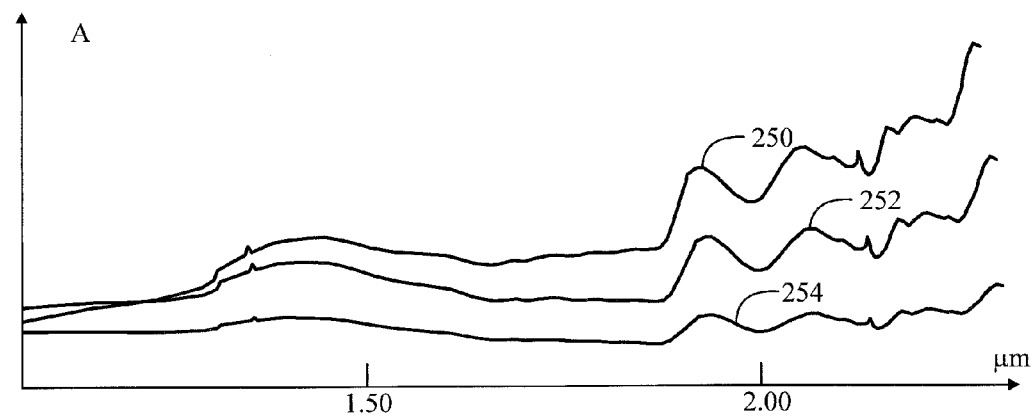
FIG. 2B shows corrected attenuation curves.

FIG. 2B illustrates the disturbance the coloring materials cause to the attenuation curve 220. The first curve 252 represents attenuation of a measured object without coloring substances. The second curve 250 represents attenuation of a measured object with one kind of mixture of coloring substances. The third curve 254 represents attenuation of a measured object with second kind of mixture of coloring substances. It can be seen that the curves 250, 252, 254 have shifted from each other and they have a tilting angle therebetween which may also have a wavelength dependence.

The attenuation may then be expressed as $A_t=(as_o+as_w+as_c+aa_o+aa_w+aa_c)$ where $as_o$ is a scattering coefficient of other substances, $as_c$ is a scattering coefficient of water, $as_w$ is a scattering coefficient of cellulose, $aa_o$ is an absorption coefficient of other substances, $aa_w$ is an absorption coefficient of water and $aa_c$ is an absorption coefficient of cellulose. Since the coefficients $as_o+as_w+as_c+aa_o+aa_w+aa_c$ are wavelength dependent, the derivative or difference quotient of the optical power as a function of wavelength depends on the scattering and absorption coefficients $as_o$ and $aa_o$, irrespective whether the rest of the coefficients $as_w$, $as_c$, $aa_w$ and $aa_c$ are constant or variable. The value of the scattering and absorption coefficients $as_o$ and $aa_o$ depends on the coloring substances which comprise the other substances in paper, for example. This is why the measurement of paper comprising coloring substances such as ink on the surface or inside the sheet faces problems in the prior art. However, it is possible to determine the general dependence of attenuation with respect to wavelength caused by the coloring substances.

The measuring unit 106 determines the general dependence of attenuation with respect to wavelength in the environment of the measured optical bands in water and cellulose absorption bands 200, 204, 202, 206. The general dependence may be determined by measuring attenuations at the two or more predetermined separate optical bands 208, 210, 212, 214 apart from the predetermined bands 200, 202, 204, 206 associated with water and cellulose. The general dependence of attenuation means a basic behavior of an attenuation curve 220 without absorption peaks of water and cellulose. Hence, it includes the disturbance caused by the coloring substances in the spectrum. For example, if the measuring unit 106 measures the water dependent value in a band 202 and the cellulose dependent value in a band 206, the measurement unit 106 may measure the attenuations taking into account the coloring substance(s) in two separate optical bands 212 and 214. The optical band 202 may comprise a wavelength about 1927 nm (5189.5 cm$^{-1}$), the optical band 206 may comprise a wavelength about 2108 nm (4743.1 cm$^{-1}$), the optical band 212 may comprise a wavelength about 1800 nm (5555 cm$^{-1}$) and the optical band 214 may comprise a wavelength about 2250 nm (4444 cm$^{-1}$).

The measuring unit 106 may determine the general dependence of attenuation with respect to wavelength as a desired type of function the parameters of which are based on the attenuation values at the measured wavelengths 208, 210, 212, 214 apart from the predetermined bands 200, 204, 202, 206 related to water and cellulose. In an embodiment, the type of function may be a linear function $A_c=b\lambda+c$, where $A_c$ is attenuation associated with coloring substances, $\lambda$ is a wavelength, b is a first parameter and c is a second parameter. The parameters b and c may be determined by requiring the linear function (=straight line) 216 pass through the measured points in the optical bands 212 and 214 outside the absorption bands of water and cellulose.

In an embodiment, the baseline of the general dependence of attenuation may comprise a piecewise linear function comprising at least two linear functions. In such a case, the curve of the general dependence of attenuation may be continuous but the slope may vary in different pieces. Each piece may range from one predetermined wavelength to another predetermined wavelength related to optical bands apart from the attenuation peaks of water and cellulose.

In an embodiment, the type of function may also be a non-linear elementary or non-elementary function $f(\lambda)$. An example of non-linear elementary function is a polynomial function the degree of which is different from 1 and 0. In a similar manner, any function $f(\lambda)$ may be required to pass through the measured points 212, 214. A corresponding treatment may be applied to optical bands 208, 200, 204 and 210 where the optical bands 208 and 210 outside the attenuation peaks of water and cellulose are used to define parameters of the desired function. The optical band 208 may comprise a wavelength about 1300 nm (7700 cm$^{-1}$), and the optical band 210 may comprise a wavelength about 1650 nm (6040 cm$^{-1}$). The optical band 200 may comprise a wavelength about 1450 nm (6900 cm$^{-1}$), and the optical band 204 may comprise a wavelength about 1600 nm (6250 cm$^{-1}$). In an embodiment, at least one predetermined separate optical band 218 for determining the function may also reside between any absorption bands 202, 206 of water and cellulose. The bandwidth of the measured bands may vary from about 1 nm to 100 nm, for instance.

In an embodiment, the determination of the general dependency may be based on measurement with any of at least two of the bands 208, 210, 212, 214 and 218, for example.

The measuring unit 106 may measure the general dependence of attenuation on the basis of at least two optical bands. One band 214 may be such that each of its wavelengths is longer than any of the wavelengths of the predetermined optical bands 202, 206 associated with water and cellulose. Another band 218 may be such that each of its wavelengths is between a predetermined optical absorption band 202 of water and a predetermined optical absorption band 214 of cellulose. A third possible optical band 212 is such that each of its wavelengths is shorter than any of the wavelengths of predetermined optical absorption bands 202, 206 of water and cellulose. The measurement may be performed in a similar manner in the optical bands 208, 200, 204 and 210.

The measuring unit 106 may form corrected water and cellulose dependent values Awc, Acc by removing the general dependence of attenuation from the water and cellulose dependent values Aw, Ac. A corrected water dependent value Awc may be integrated over a measured band $\lambda 1$ to $\lambda 2$, $Awc=\int_{\lambda 1}^{\lambda 2}(f_s(x)-f_d(x))dx$, where the optical band 200 related to water is from $\lambda 1$ to $\lambda 2$, $f_s(x)$ is the optical attenuation distribution in the optical band 200, $f_d(x)$ is the desired function determined by the measured points 212 and 214 such that it gives an estimated value for attenuation in each wavelength in the optical bands 200 and 204. A corrected cellulose dependent value Acc may be expressed in a mathematical form as $Acc=\int_{\lambda 1}^{\lambda 2}(f_s(x)-f_d(x))dx$, where the optical band 206 related to cellulose is from $\lambda 1$ to $\lambda 2$, $f_s(x)$ is the optical attenuation distribution in the optical band 206, $f_d(x)$ is the desired function determined by the measured points 212 and 214. The integration may take place automatically in the detector element or it may be computed in the measuring unit. A corresponding process may be applied to measurements of optical bands 208, 200, 204 and 210. The measurement may be performed in a similar manner in the bands 208, 200, 204 and 210. In general, the general dependence may be used to extrapolate or interpolate a value for attenuation in an optical band related to water and cellulose. In an embodiment, the measuring unit 106 may form each corrected water value Awc as a difference between a value Awf formed on the basis of the known type of function for a predetermined optical absorption band 202 of water and a corresponding water dependent value Aw. The value Alf may be formed by setting the optical band 200, 202, 204, 206 as an argument for the known type of function, $f(\Delta\lambda_k)=Alf_k$, where k is an index of the predetermined optical band. In an embodiment, the measuring unit 106 may form each corrected cellulose value Acc as a difference between a value Acf formed on the basis of the known type of function for a predetermined optical absorption band 206 of cellulose and a corresponding cellulose dependent value Ac. In a mathematical form the corrected water value Awc may be expressed as Awc=Aw−Awf. In a mathematical form the corrected cellulose value Acc may be expressed as Acc=Ac−Acf. The measurement may be performed in a similar manner in the bands 208, 200, 204 and 210. For example, Awf for the optical band 200 may be computed as Awf (200)= (a1+r(a2−a1)), where Awf(200) refers to Awf in the optical band 200, k is a coefficient, a1 is the value of attenuation in the band 208 and a2 is the attenuation in the band 210. The coefficient r may be a ratio I/L of distance I between the optical bands 208 and 200 and distance L between the optical bands 208 and 210. In other cases, Awf and Acf may be computed in a similar manner.

The measuring unit 106 may form a moisture value Mv on the basis of at least one corrected moisture dependent value Awc and at least one corrected cellulose dependent value Acc. The moisture value may be formed by dividing a corrected moisture dependent value Awc and a corresponding corrected cellulose dependent value Acc. The division may further be multiplied with a predetermined coefficient k in order to have the moisture value, Mv=k*Awc/Acc. The coefficient k may be determined by test measurements of predetermined samples having known amounts of at least one coloring substance, cellulose and water i.e the moisture value is also known beforehand. The corrected cellulose and moisture dependent values correspond to each other if they have been corrected with the same general dependence of attenuation i.e. using the same baseline correction. In order to reduce noise, a plurality of moisture measurements based on the measurements of the same optical bands may be averaged. Correspondingly if a plurality of moisture values may be formed on the basis of measurements with various optical bands, an average moisture value of the measurements may be formed.

In an embodiment, the moisture value may be formed by giving coefficients to the measurements in different optical bands. Hence, the moisture value may be formed on the basis of the at least one moisture dependent value, the at least one cellulose dependent value, and the general dependence of attenuation. The general dependence of attenuation compensates for the spectral disturbance of the at least one coloring substance. An example of an algorithm may be as follows:

$$X=(a_0+a_1A_1+a_2A_2+a_3A_3+a_4A_4)/(b_0+b_1A_1+b_2A_2+b_3A_3+b_4A_4),$$

where $A_1$ refers to a measurement of general dependence, $A_2$ refers to a measurement in an optical band associated with a water absorption peak, $A_3$ refers to a measurement in an optical band associated with a cellulose absorption peak and $A_4$ refers to a measurement of general dependence. $A_1$ may be measured at about 1805 nm, $A_2$ may be measured at about 1945 nm, $A_3$ may be measured at about 2110 nm and $A_4$ may be measured at about 2250 nm. The numerator may be interpreted to represent a corrected water dependent value and the denominator may be interpreted to represent a corrected cellulose dependent value. The coefficients $a_0$, $a_1$, $a_2$, $a_3$, $a_4$ and $b_0$, $b_1$, $b_2$, $b_3$, $b_4$ may be determined on the basis of test measurements with predetermined samples, for example. In general, the variable X may have at least two terms in the numerator and in the denominator: $X=(a_0+ \ldots +a_NA_N)/(b_0+ \ldots +b_NA_N)$, where N is the number of the terms and N is at least 1. The variable X may be the moisture value directly.

However in an embodiment, the variable X and values of measured reference samples of predetermined moisture content may be matched together using a polynomial fitting. The number of coefficients $d_0 \ldots d_M$ depends on the degree M of the fitting polynomial which may be at least one. The coefficients $d_0 \ldots d_M$, in turn, may be determined on the basis of test measurements of predetermined samples. The degree of the polynomial may be 2, for example. Then the moisture value MOI may be computed to be: $MOI=d_0+d_1X+d_2X^2$.

Figure 2C:
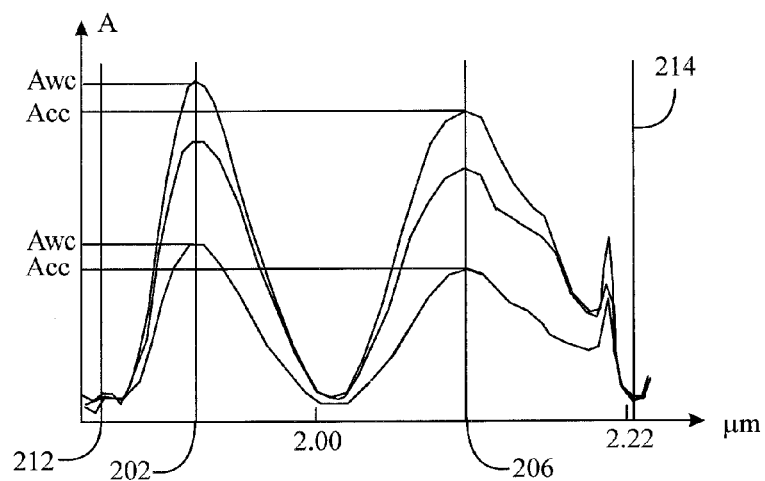
FIG. 2C presents attenuations of the measured object with various amounts of different coloring substances.

FIG. 2C presents attenuations of the measured object 100 with various amounts of different coloring substances as a function of wavelength after the correction with the general dependence of attenuation. However, the moisture level in these measurements has been about the same. The correction may correspond to a rotation of coordinates with an angle of a slope of the line 216 connecting the points of the optical bands apart from the absorption bands of water and cellulose. The rotation angle may be defined by the coefficient b of the linear function $A_c=b\lambda+c$. Alternatively or additionally, the correction may correspond to parallel displacement of the curve 220 in a vertical direction. The parallel displacement may be defined by the coefficient c in the linear function $A_c=b\lambda+c$. It may be noticed that the absorption peaks of water and cellulose behave similarly and actually the ratio between the corrected values Awc and Acc remains practically constant.

Figure 3:
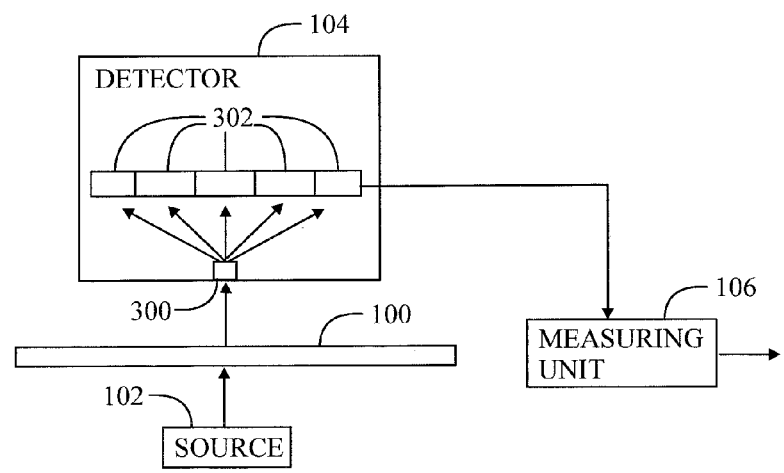
FIG. 3 shows a measuring system with a dispersing element.

FIG. 3 presents an embodiment where the detector 104 may comprise a dispersing component 300 which disperses the optical radiation into a spectrum of different optical bands $\Delta\lambda1$ to $\Delta\lambda M$ and a plurality of detector elements 302. The dispersing component 300 may comprise a prism or an optical grating. The detector 104 may comprise a spectrometer. The detector elements 302 may form an array or a matrix. The detector elements 302 may form a InGaAs (Indium Gallium Arsenide), extended InGaAs, HgCdTe (Mercury Cadmium Telluride), PbS (Lead Sulfide), PbSe (Lead Selenide) sensor for the infrared light, for example. Each of the detector elements 302 receives one of the optical bands of the dispersed optical radiation and is responsive thereto by outputting an electrical signal corresponding to an optical power of the optical band. The electrical signals may be fed to the measuring unit 106. An electrical signal from a suitable detector element 302 may alone be a signal relating to data on attenuation in a measured band. Alternatively, signals from a plurality of detector elements 302 may comprise information on one measured optical band.

Figure 4:
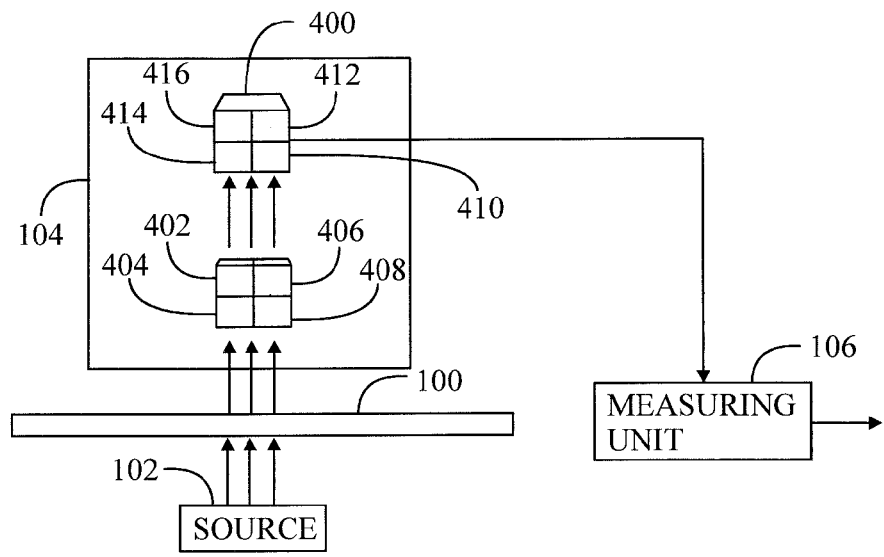
FIG. 4 shows a measuring system comprising a multichannel detector with interference filters.

FIG. 4 presents an embodiment where the detector 104 may comprise a multichannel detector 400 and an optical interference filter 402, 404, 406, 408 for each channel 410, 412, 414, 416 of the multichannel detector 400. The number of channels is at least four. At least one optical interference filter 402 may have one or more predetermined optical pass bands associated with maximum absorption of water. At least one optical interference filter 404 may have one or more predetermined optical pass bands associated with maximum absorption of cellulose. At least one optical interference filter 406 may have one or more predetermined separate optical pass bands apart from the predetermined optical absorption bands of water and cellulose. At least one further optical interference filter 408 may also have one or more predetermined separate optical pass bands apart from the predetermined optical absorption bands of water and cellulose. At least one optical pass band of the interference filter 408 is different from the at least one pass band of the interference filter 406. The channels 410 to 416 may feed their responses to the measuring unit 106 which processes the detected optical bands as described above.

A typical bandwidth $\Delta\lambda$ of a pass band of an interference filter is between 1 nm to 100 nm for example. The bandwidth may be selected freely. A middle wavelength of the pass band may be adjusted freely such that a suitable measured optical band may be passed to the detector 104.

Figure 5:
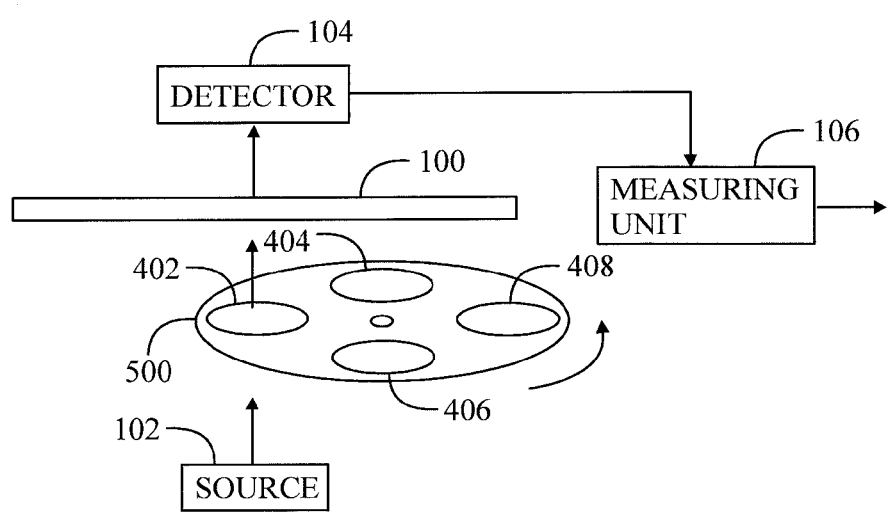
FIG. 5 shows a measuring system with revolving interference filters.

FIG. 5 presents an embodiment which utilizes a revolving interference filter disc 500. The optical source is a broad band optical source capable of outputting all measured bands of optical radiation. The detector 104 is capable of outputting an electrical signal relative to an optical power it receives. The disc 500 may have at least four interference filters 402, 404, 406, 408 each of which is capable of passing one measured optical band through. When the disc 500 is rotating, the interference filters 402, 404, 406, 408 pass the measured optical bands towards the measured object 100 one after another. The detector 104 correspondingly detects the measured optical bands one after another. Electrical signals related to the detected optical bands may be fed to the measuring unit 106 which processes the detected optical bands as described above.

Figure 6:
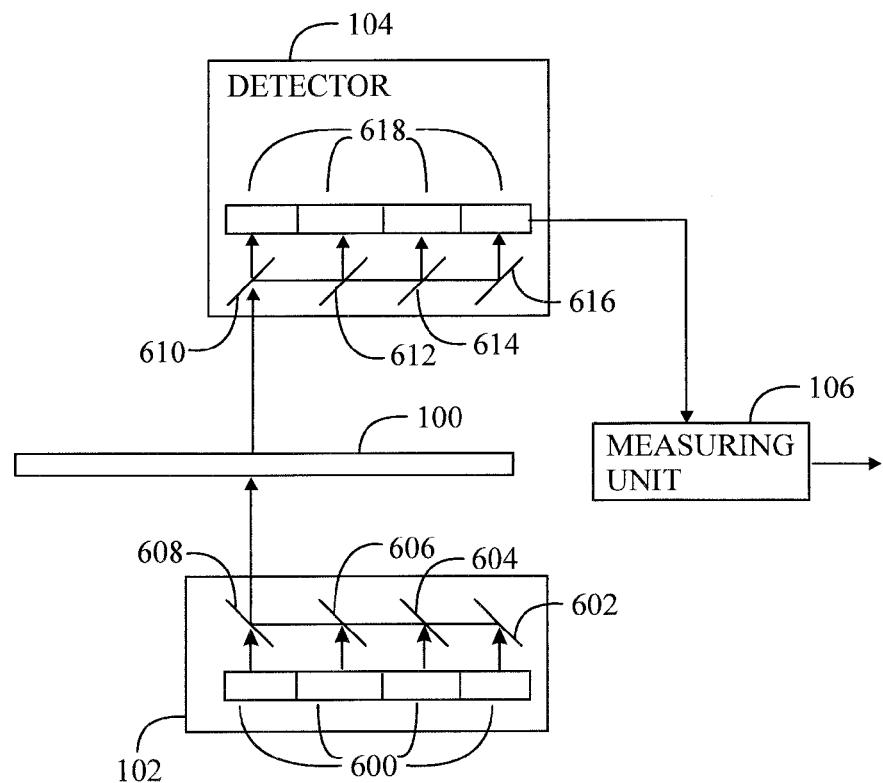
FIG. 6 shows a measuring system with a plurality of narrow band optical sources and detection utilizing beam splitters.

FIG. 6 illustrates an embodiment which utilizes a group of optical source elements 600 which have a narrow optical output band. The optical source elements 600 may be lasers or LEDs having the wavelengths used in the measurement. The optical source 106 may have a reflector 602 such as a mirror for one optical source element in periphery, and beam splitters 604, 606, 608 for the rest of the optical source elements 600. The beam splitters 604 to 608 function as beam combiners such that all optical bands from the different optical source elements 600 are directed to the same section of the measured object 100.

The detector 106 may have a group of detector elements 618 and a reflector 616 such as a mirror for one optical detector element in periphery, and beam splitters 610, 612, 614 for the rest of the optical detector elements 618. The beam splitters 610 to 614 split the measured beam into different measured optical bands and direct each band to one detector element 618.

Instead of a plurality of narrow band optical sources a broadband optical source may be used. If a broadband optical source is used, the mirror 602 and the beam splitters 604 to 608 may not be needed. Still, the detector 104 may remain the same as in FIG. 6.

If a plurality of narrow band optical sources 600 are used like in FIG. 6, the detector 104 may be similar to that presented in FIG. 3, i.e. the detector 104 comprises a spectrometer.

In an embodiment, at least one optical source may sweep over at least one measured wavelength band.

Figure 7A:
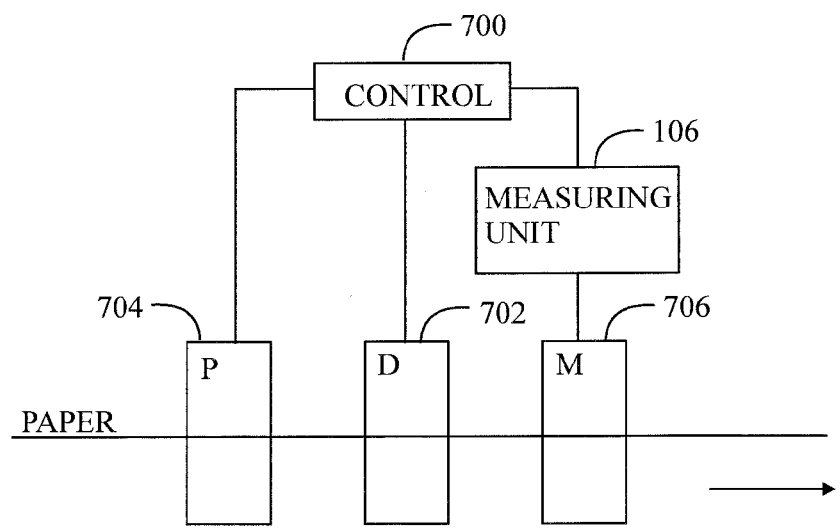
FIG. 7A illustrates control of a printing process.

FIG. 7A illustrates an embodiment where the measurement of moisture is used to control at least one process. In an embodiment, a measuring system 706 comprising the optical source 102 and the detector 104 feeds the measured signals to the measuring unit 106 which feeds the measured moisture value to the controller 700 which may control a printing process 702 and/or a drying process 704. The measuring unit 106 may be a part of the controller 700 or a separate entity.

Figure 7B:
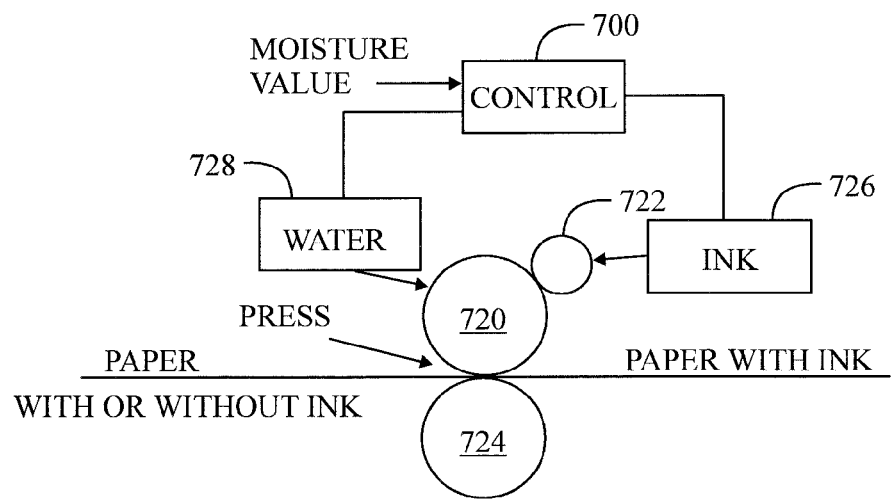
FIG. 7B illustrates a printing process.

In a printing process 704 which is illustrated in FIG. 7B coloring substance such as ink is transferred to a surface of paper which acts as the measured object 100. A purpose of the printing process 704 may be to reproduce text and/or images. In a typical printing process, ink is fed from an ink container 726 to an ink roller 722. A printing cylinder 720, in turn, may receive ink from an ink roller 722 and transfer the ink to printing press through which paper is fed. In the press, the ink is transferred from a printing cylinder 722 onto a surface of a paper by pressing the paper in contact with a printing cylinder 720 by an impression cylinder 724, for example. During printing, water from a water container 728 may be added to the ink. After the ink has been transferred on the surface of the paper, it may be dried by the drying process. The controller 700 may control the input of ink from the ink container 726 to the printing process on the basis of the moisture value. In a similar manner, the controller 700 may control the input of water from the water container 728 to the printing process on the basis of the moisture value.

Figure 7C:
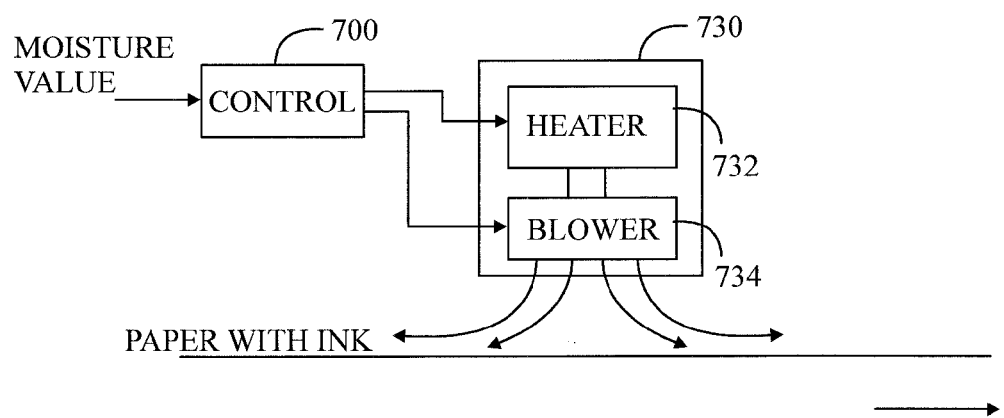
FIG. 7C illustrates a drying process.

FIG. 7C illustrates a drying process. For instance, in a heatset web offset printing ink and paper may be dried such that a drier 730 blows hot air to the paper. This drying process may be called forced-air heating. The drying power may be increased by increasing temperature of the hot air in a heater 732. The drying power may be decreased by decreasing temperature of the hot air in a heater 732. Additionally or alternatively, the hot air flow [$m^3/s$] may be increased or decreased by a blower 734 to change the drying power. If too high drying power is used, paper becomes rough and/or wrinkled and it surface doesn't look good. Additionally, the too dry papers are statically electric causing them to adhere to each other which makes their handling difficult. If, on the other hand, too low drying power is used, the ink does not become dry enough and it spreads unnecessarily spoiling the printing quality. In a more serious case, the not dry enough ink messes up everything. Hence, it is useful to optimize the drying power irrespective of the drying process used. The required drying power in any drying process depends on the moisture content of the ink and paper.

Figure 8:
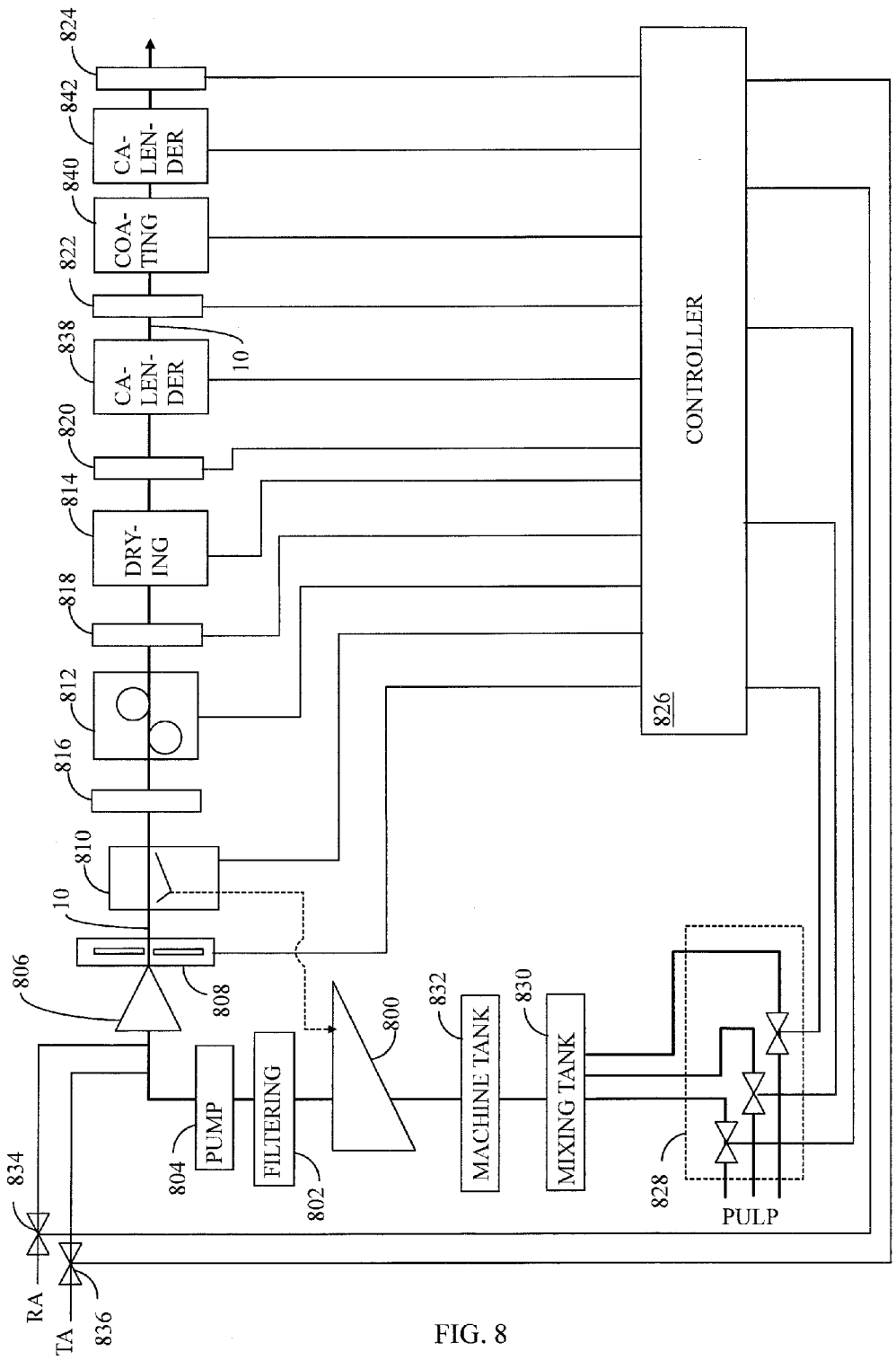
FIG. 8 illustrates a paper machine.

FIG. 8 shows the principle structure of a paper machine. A pulp flow or a plurality of pulp flows may be fed into the paper machine through a wire pit 800, which is usually preceded by a mixing tank 830 for pulp flows and a machine tank 832. The pulp may contain coloring substances which may be traces of coloring substances from colored paper or recycled paper added to the pulp on purpose. Machine pulp is batched for a short circulation by a weight control or a grade change program. The mixing tank 830 and the machine tank 832 may also be replaced by a separate mixing reactor (not shown in FIG. 8) and the batching of machine pulp is controlled by feeding each pulp flow separately by means of valves or some other flow regulating means 828. In the wire pit 800, the machine pulp is mixed with water to provide the short circulation (a broken line from a former 810 to the wire pit 800) with a desired consistency. From the pulp thus produced, it is possible to remove sand (hydrocyclones), air (deaeration tank) or other rough material (pressure screen) by cleaning equipment 802, and pulp is pumped by means of a pump 804 into a head box 806. Before the head box 806, if desired, a filler TA, such as kaolin clay, calcium carbonate, talc, chalk, titanium oxide, silica, etc., and/or a retention agent RA, such as inorganic, natural organic or synthetic water-soluble organic polymers may be added to the pulp. The filler may be used to improve formation, surface properties, opacity, brightness and printability and to reduce manufacturing costs. The retention agents RA, for their part, increase the retention of fines and fillers and simultaneously speed up the de-watering in a manner known per se. Both the fillers and the retention agents thus affect the surface topography of the web and the paper. With TA and/or RA at least one coloring substance may be added to the pulp.

From the head box 806, the pulp is fed through a slice 808 of the head box into the former 810, which may be a four-drinier or a gap former. In the former 810, the web 10 is dewatered and ash, fines and fibres are removed into the short circulation. In the former 810, the pulp is fed as a web 10 onto the wire, and the web 10 is preliminarily dried and pressed in a press 812. The web 10 is primarily dried in a drying section

814. There is usually at least one measuring part 816 to 824, by which for instance the surface topography of the web 10 can be measured.

A paper machine, which in this application refers to both paper and cardboard machines and also to pulp manufacturing machines, may also comprise, for instance, a precalender 838, a coating part/section 840 and/or a post-calender 842. However, there is not necessarily any coating section 840, and in that case there are not necessarily more than one calender 838, 842. In the coating section 840, a coating colour, which may contain for example kaolin, chalk or carbonate, starch, and/or latex, may be applied onto the paper surface. The use of coating colour usually reduces the roughness of the paper and improves glossiness.

In the calenders 838, 842, in which an uncoated or coated paper web travels between rolls that press with a desired force, the surface topography of the paper, such as roughness, can be changed. The calender 838, 842 may also affect the thickness and/or gloss of the paper. In the calender 838, 842, the properties of the paper web may be changed by moistening the web or by means of temperature and nip load/pressure between the rolls so that the greater the press applied to the web is, the smoother and glossier the paper will become. Moistening and an increase in the temperature further reduce roughness and improve glossiness. In addition, it is obvious that the operation of a paper machine is known per se to a person skilled in the art, wherefore it is not described in more detail in this context.

FIG. 8 also shows a control system for the paper machine. Factors affecting the quality and grade change include the amount and ratio of pulp flows, amount of filler, amount of retention agent, machine velocity, amount of backwater and drying capacity. A controller 826 may control the batching of pulp flows by means of regulating valves 828, the batching of the filler TA by a valve 836, the batching of the retention agent RA by a valve 834, it may also control the size of the slice 808, the machine velocity, the amount of backwater and the drying process in block 814. The controller 826 utilizes the measuring devices 816 to 820 which comprise the detector 804 and usually also the optical radiation source 802 for monitoring moisture. The controller 826 may also measure the web 10 properties elsewhere (e.g. at the same points where controls are carried out).

The controller 826 may be considered as a control arrangement based on automatic data processing of the paper machine, or as a part thereof. The controller 826 may receive digital signals or convert the received analog signals to digital signals. The controller 826 may comprise a microprocessor and memory and process the signal according to a suitable computer program. The controller 826 may be based on a PID (Proportional-Integral-Derivative), MPC (Model Predictive Control) or GPC (General Predictive Control) control, for example.

Figure 9:
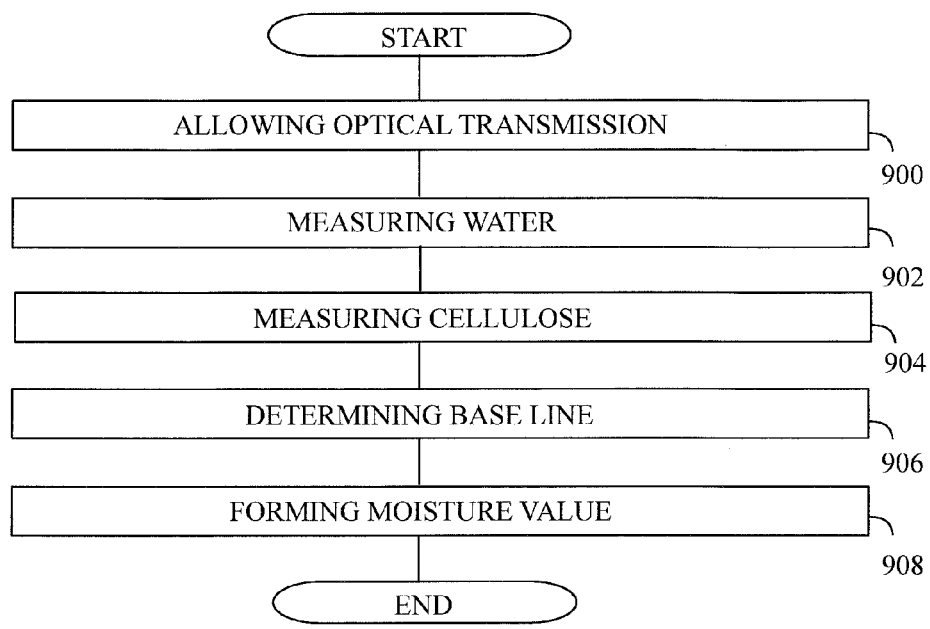
FIG. 9 shows a flow chart of the measuring method.

FIG. 9 presents a flow chart of the measurement. In step 900, allowing optical radiation propagate through a measured object comprising cellulose material and coloring substance. In step 902, measuring at least one water dependent value on the basis of attenuation of the optical radiation transmitted through the measured object in one or more predetermined optical absorption bands of water. In step 904, measuring at least one cellulose dependent value on the basis of attenuation of the optical radiation transmitted through the measured object in one or more predetermined optical absorption bands of cellulose. In step 906, determining general dependence of attenuation of the optical radiation transmitted through the measured object with respect to wavelength by measuring attenuations at two or more predetermined separate optical bands known to include spectral disturbance caused by the at least one coloring substance, the separate optical bands being apart from the predetermined optical bands associated with water and cellulose. In step 908, a moisture value is formed on the basis of at least one moisture dependent value, at least one cellulose dependent value, and the general dependence of attenuation for compensating for the spectral disturbance of the at least one coloring substance.

Figure 10:
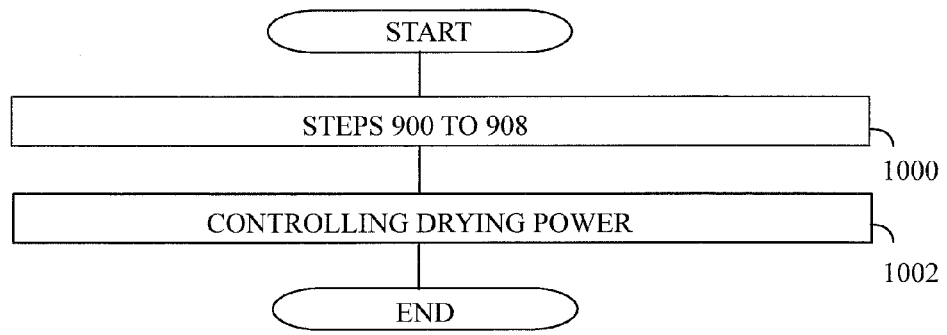
FIG. 10 shows a flow chart of the controlling method of a drying process.

FIG. 10 presents a flow chart of a control of a drying process. The step 1000 comprises the steps of FIG. 9. In step 1002, drying power in a drying process is controlled on the basis of the moisture value.

Figure 11:
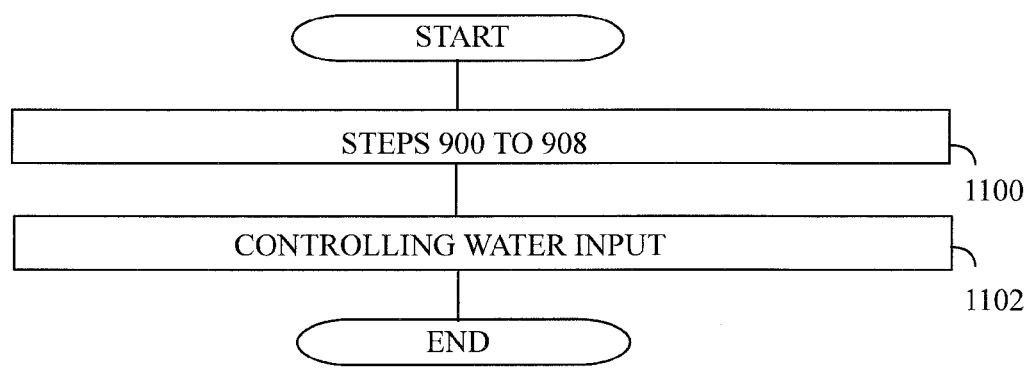
FIG. 11 shows a flow chart of the controlling method a printing process.

FIG. 11 presents a flow chart of a control of a printing process. The step 1100 comprises the steps of FIG. 9. In step 1102, water input in a printing process is controlled on the basis of the moisture value.

The measuring unit 106 and the controllers 700, 826 capable of performing the steps presented in at least one of FIGS. 9 to 11 may be implemented as an electronic digital computer, or a circuitry which may comprise a working memory (RAM), a central processing unit (CPU), and a system clock. The CPU may comprise a set of registers, an arithmetic logic unit, and a controller. The controller or the circuitry is controlled by a sequence of program instructions transferred to the CPU from the RAM. The controller may contain a number of microinstructions for basic operations. The implementation of microinstructions may vary depending on the CPU design. The program instructions may be coded by a programming language, which may be a high-level programming language, such as C, Java, etc., or a low-level programming language, such as a machine language, or an assembler. The electronic digital computer may also have an operating system, which may provide system services to a computer program written with the program instructions.

The measuring unit 106 and the controllers 700, 826 may comprise circuitries which refer to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present.

As a further example, the term 'circuitry' would also cover an implementation of merely a processor (or multiple processors) or a portion of a processor and its (or their) accompanying software and/or firmware.

An embodiment provides a computer program embodied on a distribution medium, comprising program instructions which, when loaded into an electronic apparatus, are configured to control the apparatus to execute the embodiments described above.

The computer program may be in source code form, object code form, or in some intermediate form, and it may be stored in some sort of carrier, which may be any entity or device capable of carrying the program. Such carriers include a record medium, computer memory, read-only memory, and a software distribution package, for example. Depending on the processing power needed, the computer program may be executed in a single electronic digital computer or it may be distributed amongst a number of computers.

The apparatuses may also be implemented as one or more integrated circuits, such as application-specific integrated circuits ASIC (Application Specific Integrated Circuit). Other hardware embodiments are also feasible, such as a circuit built of separate logic components. A hybrid of these different implementations is also feasible. When selecting the method of implementation, a person skilled in the art will consider the requirements set for the size and power consumption of the apparatus, the necessary processing capacity, production costs, and production volumes, for example.

It will be obvious to a person skilled in the art that, as technology advances, the inventive concept can be implemented in various ways. The invention and its embodiments are not limited to the examples described above but may vary within the scope of the claims.

The invention claimed is:

1. An apparatus for measuring an object comprising cellulose material and at least one coloring substance including printing ink, wherein the apparatus comprising a detector and a measuring unit;

the detector being configured to receive optical radiation transmitted through the measured object within the optical band ranging from 1.8 μm to 2.25 μm and being responsive to one or more predetermined optical absorption bands of water, one or more predetermined optical absorption bands of cellulose and two or more separate optical bands known to include spectral disturbance caused by the at least one coloring substance, the separate optical bands being apart from the predetermined optical bands associated with water and cellulose, at least two of the separate optical bands being on both sides of a predetermined optical band associated with water and at least two of the separate optical bands being on both sides of a predetermined optical band of cellulose;

the measuring unit being configured to, on the basis of responses of the detector, measure at least one water dependent value on the basis of attenuation of the optical radiation in the one or more predetermined optical absorption bands of water, measure at least one cellulose dependent value on the basis of attenuation of the optical radiation in the one or more predetermined optical absorption bands of cellulose, determine general dependence of attenuation with respect to wavelength including spectral disturbance caused by the at least one coloring substance as a desired type of function by measuring attenuations at the measured wavelengths apart from the predetermined bands associated with water and cellulose;

form each of at least one corrected water value on the basis of the desired type of function and a corresponding water dependent value, and form each of at least one corrected cellulose value on the basis of the desired type of function and a corresponding cellulose dependent value, and form a moisture value on the basis of at least one corrected moisture value and at least one corrected cellulose value, for compensating for the spectral disturbance of the at least one coloring substance.

2. The apparatus of claim 1, the apparatus comprising an optical source configured to transmit optical radiation through a measured object.

3. The apparatus of claim 1, the measuring unit being configured to form corrected water and cellulose dependent values by removing the general dependence of attenuation from the water and cellulose dependent values for compensating for at least the disturbance of the at least one coloring substance on the spectrum, and form a moisture value on the basis of at least one corrected moisture dependent value and at least one corrected cellulose dependent value.

4. The apparatus of claim 1, wherein the measuring unit being configured to measure the general dependence of attenuation on the basis of at least two of the following optical bands: a band each wavelength of which being longer than any of the wavelengths of the predetermined optical absorption bands of water and cellulose, and a band each wavelength of which being shorter than any of the wavelengths of predetermined optical absorption bands of water and cellulose.

5. The apparatus of claim 4, wherein the measuring unit being configured to measure the general dependence of attenuation additionally on the basis of at least one band each wavelength of which being between a predetermined optical absorption bands of water and cellulose.

6. The apparatus of claim 1, wherein the detector comprising a dispersing component configured to disperse the optical radiation into optical bands comprising the measured optical bands, and detector elements being configured to receive the optical bands and being responsive thereto.

7. The apparatus of claim 1, wherein the detector comprising a multichannel detector and an optical interference filter for each channel; at least one optical interference filter having one or more predetermined optical pass bands associated with maximum water absorption, one or more predetermined optical pass bands associated with maximum cellulose absorption and two or more separate optical pass bands apart from the predetermined optical bands; and the channels being configured to feed their responses to the measuring unit.

8. A system, comprising the apparatus of claim 1, wherein the system comprising at least one drier and a controller, the drier being configured to dry the measured object and the controller being configured to control the drying power of the at least one drier on the basis of the moisture value.

9. A system, comprising the apparatus of claim 1, wherein the system comprising a printing process and a controller, the controller being configured to control water input in the printing process on the basis of the moisture value.

10. A method for measuring an object comprising cellulose material and at least one coloring substance including printing ink, the method comprising allowing optical radiation being transmitted through a measured object;

measuring at least one water dependent value on the basis of attenuation of the optical radiation transmitted through the measured object in one or more predetermined optical absorption bands of water;

measuring at least one cellulose dependent value on the basis of attenuation of the optical radiation transmitted through the measured object in one or more predetermined optical absorption bands of cellulose within the optical band ranging from 1.8 μm to 2.25 μm;

determining general dependence of attenuation of the optical radiation transmitted through the measured object with respect to wavelength, by measuring attenuations in two or more predetermined separate optical bands known to include spectral disturbance caused by the at least one coloring substance, as a known type of function, at least two of the separate optical bands being on both sides of a predetermined optical band associated with water and at least two of the separate optical bands being on both sides of a predetermined optical band of cellulose; and forming each of at least one corrected water value on the basis of the desired type of function and a corresponding water dependent value, and forming each of at least one corrected cellulose value on the basis of the desired type of function and a corresponding cellulose dependent value; and forming a moisture value on the basis of at least one corrected moisture value and at least one corrected cellulose value for compensating for the spectral disturbance of the at least one coloring substance.

11. The method of claim 10, the method further comprising forming corrected water and cellulose dependent values by removing the determined general dependence of attenuation from the water and cellulose dependent values for compensating for at least the disturbance of the at least one coloring substance on the spectrum; and forming a moisture value on the basis of at least one corrected moisture dependent value and at least one corrected cellulose dependent value.

12. The method of claim 10, the method further comprising measuring the general dependence of attenuation on the basis of at least two of the following optical bands: a band each wavelength of which being longer than any of the wavelengths of the predetermined optical absorption bands of water and cellulose, and a band each wavelength of which being shorter than any of the wavelengths of predetermined optical absorption bands of water and cellulose.

13. The method of claim 12, the method further comprising measuring the general dependence of attenuation additionally on the basis of at least one band each wavelength of which being between predetermined absorption optical bands of water and cellulose.

14. The method of claim 10, the method further comprising dispersing, in the detector, the optical radiation into a spectrum, and receiving and responding to an optical band of the spectrum by each detector element.

15. The method of claim 10, wherein the detector comprising a multichannel detector and an optical interference filter for each channel; at least one optical interference filter having one or more predetermined optical pass bands associated with maximum water absorption, one or more predetermined optical pass bands associated with maximum cellulose absorption and two or more separate optical pass bands in known ranges from the predetermined optical bands; and feeding, by the channels, their responses to the measuring unit.

16. A method, the method comprising the steps of claim 10 and further comprising controlling drying power in a drying process on the basis of the moisture value.

17. A method, the method comprising the steps of claim 10 and further comprising controlling water input in a printing process on the basis of the moisture value.

18. An apparatus for measuring an object comprising cellulose material and at least one coloring substance including printing ink, the apparatus comprising:

at least one processor; and at least one memory including a computer program code, wherein the at least one memory and the computer program code are configured, with the at least one processor, to cause the apparatus at least to perform allowing optical radiation propagate through a measured object comprising cellulose material and the at least one coloring substance;

measuring at least one water dependent value on the basis of attenuation of the optical radiation transmitted through the measured object in one or more predetermined optical absorption bands of water;

measuring at least one cellulose dependent value on the basis of attenuation of the optical radiation transmitted through the measured object in one or more predetermined optical absorption bands of cellulose within the optical band ranging from 1.8 µm to 2.25 µm;

determining general dependence of attenuation of the optical radiation transmitted through the measured object with respect to wavelength, by measuring attenuations in two or more predetermined separate optical bands known to include spectral disturbance caused by the at least one coloring substance, as a known type of function, at least two of the separate optical bands being on both sides of a predetermined optical band associated with water and at least two of the separate optical bands being on both sides of a predetermined optical band of cellulose; and forming each of at least one corrected water value on the basis of the desired type of function and a corresponding water dependent value, and forming each of at least one corrected cellulose value on the basis of the desired type of function and a corresponding cellulose dependent value; and forming a moisture value on the basis of at least one corrected moisture value and at least one corrected cellulose value for compensating for the spectral disturbance of the at least one coloring substance.

19. The apparatus of claim 18, wherein the computer program code, cause the apparatus to form corrected water and cellulose dependent values by removing the determined general dependence of attenuation from the water and cellulose dependent values for compensating for at least the disturbance of the at least one coloring substance on the spectrum; and form a moisture value on the basis of at least one corrected moisture dependent value and at least one corrected cellulose dependent value.

20. A system, the system comprising the apparatus of claim 18 and further comprising a drying process and a controller configured to control the drying process on the basis of the moisture value.

21. A system, the system comprising the apparatus of claim 18 and further comprising a printing process and a controller configured to control water input in the printing process on the basis of the moisture value.

* * * * *